United States Patent [19]

Nordin

[11] Patent Number: 5,094,620

[45] Date of Patent: Mar. 10, 1992

[54] ANCHORAGE SYSTEM FOR AN ARTIFICIAL TOOTH

[76] Inventor: Harald E. Nordin, Villa Amphion, CH-1822 Chernex, Switzerland

[21] Appl. No.: 556,260

[22] Filed: Jul. 20, 1990

[51] Int. Cl.⁵ ............................ A61C 5/08; A61C 5/10
[52] U.S. Cl. ..................................... 433/220; 433/223
[58] Field of Search ............... 433/173, 174, 220, 221, 433/218, 223

[56] References Cited

U.S. PATENT DOCUMENTS

| | | | |
|---|---|---|---|
| 3,557,454 | 1/1971 | Whitehill et al. | 433/220 |
| 3,602,993 | 9/1971 | Kearney | 433/218 |
| 4,253,835 | 3/1981 | Ware | 433/220 |
| 4,604,060 | 8/1986 | Weissman | 433/221 |
| 4,645,457 | 2/1987 | Goldman et al. | 433/220 |
| 4,744,756 | 5/1988 | Ross | 433/221 X |

*Primary Examiner*—Robert P. Swiatek
*Assistant Examiner*—Nicholas D. Lucchesi
*Attorney, Agent, or Firm*—Marks Murase & White

[57] ABSTRACT

The anchorage equipment for an artificial tooth comprises a cap made of a gold alloy which is adapted to be stuck onto the head of the root canal anchorage post. The porcelain build-up can be applied to this cap directly by molding. The head of the root canal anchorage post comprises a pin haaving a laterally flattened portion, and the plug-on cap has a corresponding bore provided with a flattened portion for the purpose of mutual alignment. The equipment further includes a transfer cap and a transfer pin having the same alignment feature as the above-mentioned pin and cap. For the production of an artificial tooth, first an impression is taken with the transfer cap plugged on, then a gypsum impression is prepared with the transfer pin inserted into the transfer cap, whereupon the dental technician can proceed to stick the cap onto the projecting transfer pin in order to form the porcelain crown directly on the cap. Finally, the dentist cements the finished artificial tooth including the cap to the root canal anchorage post. Such an equipment greatly facilitates and simplifies the production of an artificial tooth, and not only a shorter and substantially more acceptable procedure for the patient results, but also a reduction of expenses.

6 Claims, 2 Drawing Sheets

ANCHORAGE SYSTEM FOR AN ARTIFICIAL TOOTH

BACKGROUND OF THE INVENTION

The present invention relates to an anchorage system for an artificial tooth, comprising a root canal anchorage post, and to the use of this system for the production of an artificial tooth.

The common generally known procedure for the production of an artificial tooth first comprises the anchoring of the root canal anchorage post. Then, the dentist makes a composite build-up and cuts the resulting cone to the shape of a stub. For better anchorage of this composite build-up, root canal anchorage posts generally comprise one or several retention wings on the projecting head. After finishing the composite build-up, the dentist makes an impression thereof and hands it over to the dental technician. On the base of this impression, the dental technician produces a gypsum mould and prepares a gold alloy jacket which is produced by the lost-wax process. The porcelain build-up is moulded over this gold jacket, whereupon the build-up can be fastened to the composite build-up by means of the jacket.

Production and subsequent finishing of the composite build-up is quite laborious and causes great discomfort to the patient. Besides, preparation of the gold filling, respectively the gold jacket, is very labor-intensive and therefore, expensive.

SUMMARY OF THE INVENTION

On the background of the above method for the production of an artificial tooth, respectively the component parts of the artificial tooth, it is the object of the present invention to provide an anchorage system consisting of few, simple parts and allowing, on the other hand, a substantially more comfortable and more economical procedure for the production of an artificial tooth.

This object and still others are attained by the anchorage system of this invention wherein said equipment generally comprises a plug-on cap made of a suitable material for the porcelain build-up to be secured thereto, said plug-on cap being adapted to be plugged onto said root canal anchorage post in an aligned position, the head of said root canal anchorage post comprising a pin having a lateral flattened portion, and said plug-on cap comprising a corresponding bore having a flattened portion, and by the use of said anchorage system.

BRIEF DESCRIPTION OF THE DRAWINGS

The invention is explained in more detail hereinafter with reference to a drawing of an embodiment.

DETAILED DESCRIPTION OF THE INVENTION

Figure 1:
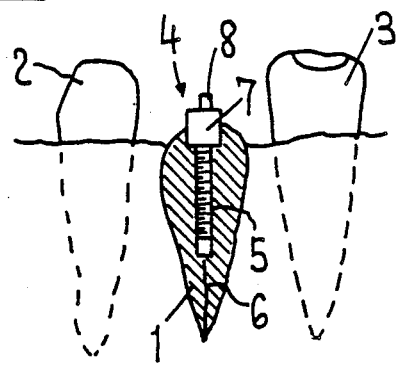
FIGS. 1 to 6 show the essential steps of the procedure for producing an artificial tooth, as well as the equipment needed therefor.
Figure 7:
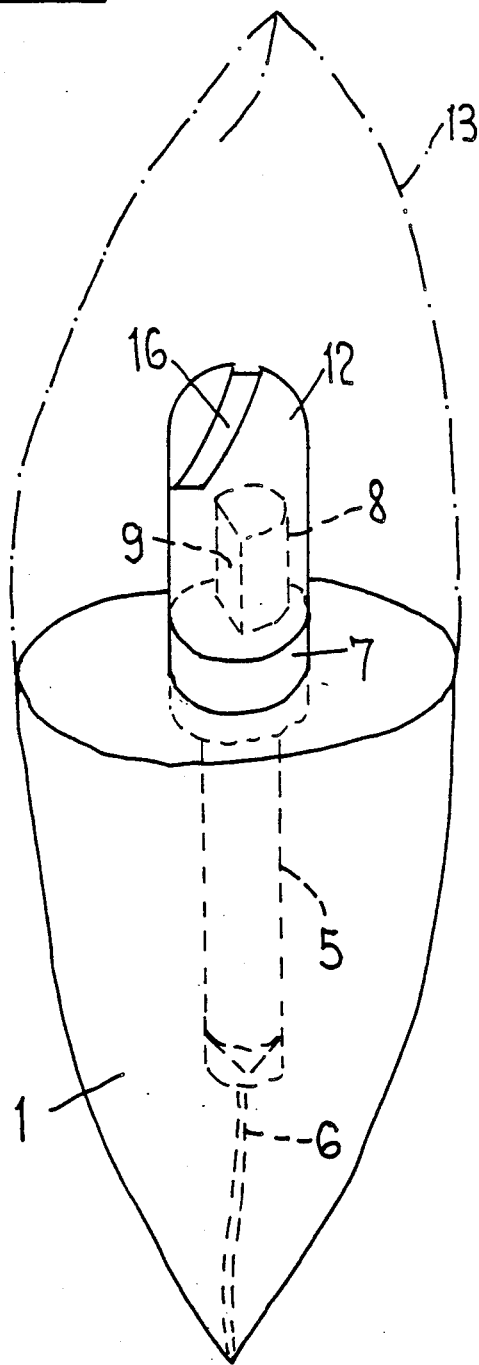
FIG. 7 shows the installed artificial tooth on an enlarged scale.

A damaged tooth 1 as well as the two schematically shown neighboring teeth 2 and 3 of a human denture — exemplified by the lower jaw — appear in FIG. 1. In the damaged tooth 1, respectively in its root canal 6, a root canal anchorage post 4 is fastened whose anchoring portion 5 is not an object of this invention and may have any desired shape. FIG. 7 shows the schematic configuration of the damaged tooth 1 and the root canal anchorage post more clearly, the latter being secured in the root canal 6 as well. The head of the root canal anchorage post consists of a cylindrical plate 7 on which a pin 8 is arranged having a laterally flattened portion 9 in order to align the parts which are to be plugged on.

Figure 2:
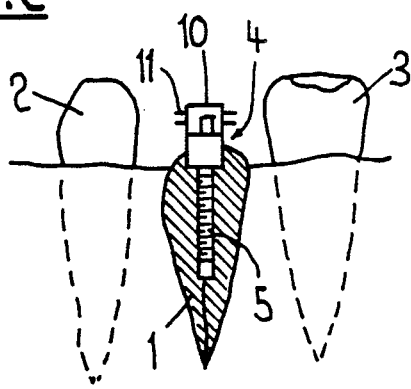
Figure 5:
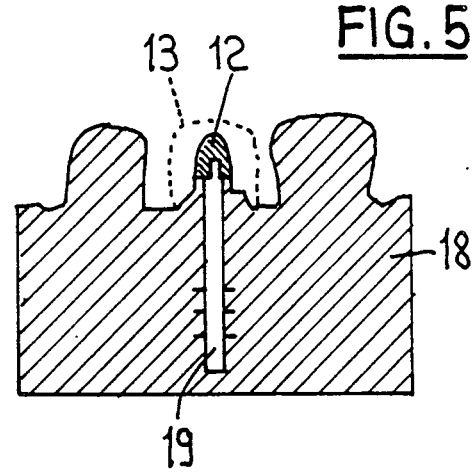
Figure 3:
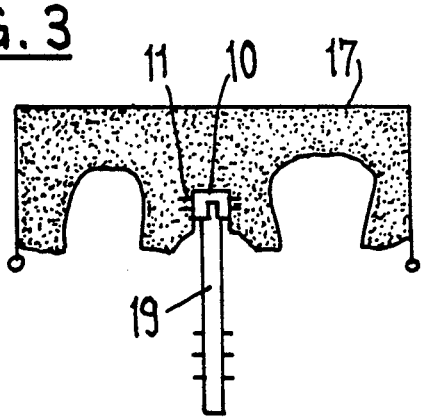
Figure 6:
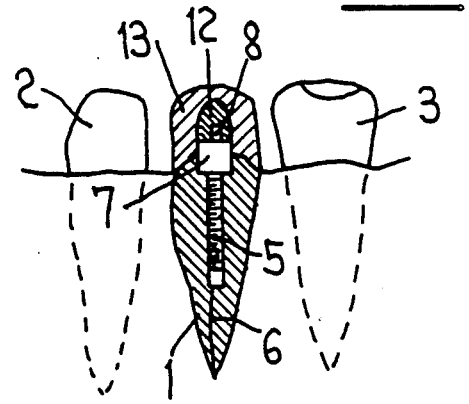
Figure 8:
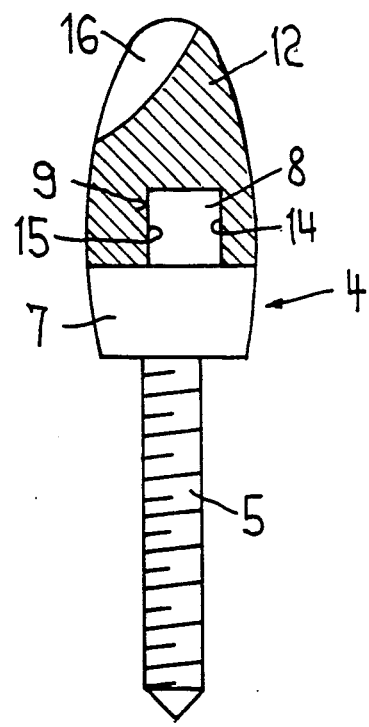
FIG. 8 shows the root canal anchorage post with the cap of the anchorage system or equipment of the invention fitted thereto.

The parts to be plugged onto flattened pin 8 are a transfer cap 10 made of plastics material, see FIG. 2, which is provided with wings 11 or similar retention means for the purpose of a better anchorage in the impression material, and a cap 12 made of a precious metal alloy mostly containing gold and palladium, or of titanium, which in any case must have the property that a porcelain crown 13 can be directly attached thereto. Cap 12 is provided with a bore 14 having a flattened portion 15 which corresponds to pin 8 in order to allow a precise and accurately aligned fit on the pin. For the purpose of a better anchorage of the porcelain crown on the cap, the latter is provided with an anchoring groove 16 in its upper section. The external shape of the cap may be either more cylindrical, as shown in FIG. 7, or more conical, as shown in FIG. 8.

Figure 4:
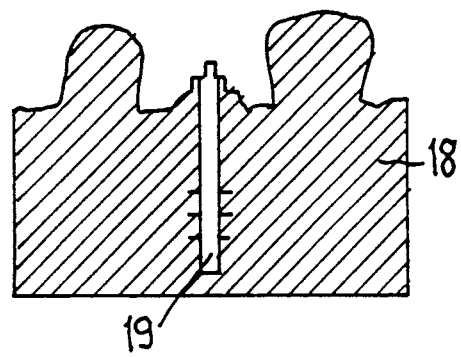

The working steps for the production of a finally fastened artificial tooth are explained herebelow with reference to FIGS. 1 to 6. After a suitable preparation as known per se, the root canal anchorage post 4 is secured in the damaged tooth, either by means of a cement or, when an accordingly shaped anchoring section is provided, without cement. The dentist then connects the prefabricated plastics transfer cap 10 onto the projecting pin of the anchorage post, and an impression 17 is subsequently taken in the patient's mouth. Afterwards, see FIG. 3, a transfer pin 19, which is also prefabricated and made of plastics material, is inserted by the dental technician into impression 17 in which the transfer cap is embedded, and a gypsum mould 18 is made of the model according to FIG. 3, as it is shown in FIG. 4. The uppermost part of the transfer pin which has the same configuration and dimensions as pin 8 on the root canal anchorage post, projects from this gypsum model. A likewise prefabricated cap 12 is plugged onto this pin, whereupon the dental technician applies the porcelain crown directly to said cap and adapts it to the neighboring teeth according to known procedures. As a last step, the dentist merely applies the artificial tooth, i.e. the porcelain crown including the cap, to the root canal anchorage post and cements it.

It is self-evident to the man skilled in the art that in contrast to the previously described known procedure, the invention provides great improvements and strongly relieves the dentist. This is due to the precisely fitting prefabricated parts on one hand, and on the other hand, to the resulting method which is substantially simplified and, most importantly, substantially more comfortable for the patient. This noticeable relief of the dentist and the simplification of the subsequent steps not only allow a more acceptable treatment for the patient, but the treatment is also expected to be substantially more economical, i.e. to reduce the production costs for an artificial tooth considerably. Moreover, manufacture of the root canal anchorage post is also rendered simpler and more economical because not only its form is much simpler, but as a consequence of the small, short pin, material may be saved. As already mentioned, the anchoring portion may have any tested and proved configuration.

What I claim is:

1. A method for anchoring an artificial tooth to a root canal, comprising the steps of:

anchoring a root canal anchorage post having a head into said root canal;

connecting a transfer cap to said head of said anchorage post;

taking an impression of said transfer cap and adjacent tooth portions;

inserting as transfer pin into said transfer cap;

making a mold thereof with said transfer pin embedded therein;

attaching a prefabricated plug-on cap, said plug-on cap being made of suitable material for a porcelain build-up to be secured thereto and adapted to be plugged onto said root canal anchorage post in an aligned position, to said transfer pin embedded in said mold;

molding the porcelain build-up directly upon said prefabricated plug-on cap; and cementing an artificial tooth including said plug-on cap to said root canal anchorage post.

2. The method of claim 1 further comprising the step of:

creating a lateral flattened portion on said pin and a corresponding bore having a flattened portion on said plug-on cap.

3. The method of claim 2 further comprising the step of:

making the same bore, having a flattened portion as said plug-on cap, on said transfer cap; and forming the uppermost portion of said transfer pin to have the same flattened portion as said plug-on cap on said head of said root canal anchorage post.

4. The method of claim 3 further comprising the step of:

prefabricating said transfer cap and pin out of plastic material.

5. The method of claim 1 further comprising the step of:

making said prefabricated plug-on cap out of a precious metal alloy.

6. The method of claim 1 wherein said making step further includes the step of using gypsum to make the mold.

* * * * *

UNITED STATES PATENT AND TRADEMARK OFFICE
CERTIFICATE OF CORRECTION

PATENT NO. : 5,094,620

DATED : March 10, 1992

INVENTOR(S) : Nordin, Harald E.

It is certified that error appears in the above-identified patent and that said Letters Patent is hereby corrected as shown below:

On the title page, Item [56] Foreign Application Priority should be shown by adding the following:

-- Foreign Application Priorty Data
July 20, 1989  European Pat. Off.....89810548.1 --.

Signed and Sealed this

Twenty-second Day of June, 1993

Attest:

MICHAEL K. KIRK

*Attesting Officer*     Acting Commissioner of Patents and Trademarks